(12) United States Patent
Cinquin et al.

(10) Patent No.: US 10,383,714 B2
(45) Date of Patent: Aug. 20, 2019

(54) DEVICE TO PREVENT URINARY LEAKAGE

(75) Inventors: Philippe Cinquin, St Nazaire les Eymes (FR); Pierren Mozer, Vincennes (FR); Hamid Lamraoui, Grenoble (FR); Agnes Bonvilain, Myans (FR); Gilberte Robain, Paris (FR)

(73) Assignee: Uromems, Grenoble (FR)

( * ) Notice: Subject to any disclaimer, the term of this patent is extended or adjusted under 35 U.S.C. 154(b) by 707 days.

(21) Appl. No.: 12/674,501

(22) PCT Filed: Aug. 7, 2008

(86) PCT No.: PCT/EP2008/060404
§ 371 (c)(1),
(2), (4) Date: Feb. 22, 2010

(87) PCT Pub. No.: WO2009/027196
PCT Pub. Date: May 3, 2009

(65) Prior Publication Data
US 2011/0124955 A1    May 26, 2011

(30) Foreign Application Priority Data
Aug. 24, 2007 (FR) ...................................... 07 57159

(51) Int. Cl.
*A61F 2/00* (2006.01)
*A61B 5/0488* (2006.01)
(Continued)

(52) U.S. Cl.
CPC ........ *A61F 2/0036* (2013.01); *A61B 5/04882* (2013.01); *A61B 5/1116* (2013.01);
(Continued)

(58) Field of Classification Search
CPC ... A61B 5/202; A61B 5/04882; A61B 5/1116; A61B 5/1118; A61B 5/1123; A61B 5/205; A61B 2562/0219; A61F 2/0004–2/0054
(Continued)

(56) References Cited

U.S. PATENT DOCUMENTS 4,721,509 A    1/1988   Craggs
6,135,945 A    10/2000  Sultan
(Continued)

FOREIGN PATENT DOCUMENTS

WO    00/15140    3/2000
WO    01/45487    6/2001
(Continued)

OTHER PUBLICATIONS

International Search Report of PCT/EP2008/060404, completed Nov. 19, 2008.
(Continued)

*Primary Examiner* — Catherine B Kuhlman
(74) *Attorney, Agent, or Firm* — Harness, Dickey & Pierce, PLC (57) ABSTRACT

The invention concerns a device to prevent urinary leakage intended to be implanted in a patient, comprising:
  compression means (1, 3, 4, 5) to compress the patient's urethra,
  electronic control means (2) to actuate the compression means (1, 3, 4, 5),
characterized in that it further comprises measurement means (7) to measure the patient's activity, coupled with the control means (2), the control means (2) functioning according to a predictive model of urinary leakage based on patient activity, so as to anticipate a possible urinary leak in relation to the measured activity of the patient.

35 Claims, 2 Drawing Sheets

(51) Int. Cl.
*A61B 5/11* (2006.01)
*A61B 5/20* (2006.01)

(52) U.S. Cl.
CPC .............. *A61B 5/202* (2013.01); *A61B 5/205* (2013.01); *A61B 2562/0219* (2013.01); *A61F 2250/0002* (2013.01)

(58) Field of Classification Search
USPC .................. 600/29–31, 37; 128/897–899
See application file for complete search history.

(56) References Cited

U.S. PATENT DOCUMENTS

| | | | |
|---|---|---|---|
| 6,638,208 B1* | 10/2003 | Natarajan et al. | 600/30 |
| 6,862,480 B2* | 3/2005 | Cohen et al. | 607/41 |
| 7,217,237 B2* | 5/2007 | Wassermann et al. | 600/29 |
| 8,121,691 B2* | 2/2012 | Gerber et al. | 607/41 |
| 2002/0062060 A1* | 5/2002 | Gross et al. | 600/30 |
| 2006/0047180 A1* | 3/2006 | Hegde et al. | 600/30 |
| 2008/0300449 A1* | 12/2008 | Gerber et al. | 600/30 |
| 2008/0300470 A1* | 12/2008 | Gerber et al. | 600/301 |
| 2009/0306460 A1* | 12/2009 | Stephens et al. | 600/30 |

FOREIGN PATENT DOCUMENTS

| | | |
|---|---|---|
| WO | 01/50833 | 7/2001 |
| WO | 03/043534 | 5/2003 |
| WO | 2006/026509 | 3/2006 |

OTHER PUBLICATIONS

Knight et al., "A New Artificial Urinary Sphincter with Condition Occlusion for Stress Urinary Incontinence: Preliminary Clinical Results", EAU Congress, 2006, p. 574-580, Paris.

Elliott et al., "An Implantable Mechanical Urinary Sphincter: A New Nonhydraulic Design Concept", Urology, 1998, v 52, p. 1151-1154.

Combrisson et al., "Comparative effects of xylazine and propofol on the urethral pressure profile of healthy dogs", Am J Vet Res, 1993, v 54, p. 1986-1989.

Hajivassiliou, C.A.; "A Review of the Complications and Results of Implantation of the AMS Artificial Urinary Sphincter"; Eur. Urol., 1999; 35(1): p. 36-44.

Knight S., S.J.; Greenwell T., Mundy A., Craggs M.; "A New Artificial Urinary Sphincter With Conditional Occlusion for Stress Urinary Incontinence—Long Term Clinical Results", in EAU Congress; 2006; Paris; vol. 50, Issue 3, pp. 574-580.

Elliott, D.S., G.W. Timm, and D.M. Barrett, "An Implantable Mechanical Urinary Sphincter: A New Nonhydraulic Design Concept", Urology, 1998. 52(6): p. 1151-4.

Van der Kooi, J.B., et al., "Time Separation Between Cough Pulses in Bladder, Rectum and Urethra in Women", J Urol, 1984. 132(6): p. 1275-8.

Combrisson, H., G. Robain, and J.P.Cotard, "Comparative Effects of Xylazine and Propofol on the Urethral Pressure Profile of Healthy Dogs"; Am J Vet Res, 1993, 54(12): p. 1986-9.

K. Bo, "Pelvic Floor Muscle Strength and Response to Pelvic Floor Muscle Training for Stress Urinary Incontinence", Neurourology and Urodynamics, 22 :654-658, 2003.

C.A. Hajivassiliou and I.G. Finlay; "Uneven Pressure Application by the Artificial Urinary Sphincter : An Explanation for Tissue Ischaemia?"; BJU International, 83 :416-419, 1999.

Z. Hamici, R. Itti, and Hampier J.; "A High-Efficiency Power and Data Transmission System for Biomedical Implanted Electronic Devices"; Meas. sci. technol., 7 :192-201, 1996.

D. K. Montague and K. W. Angermeier. Artificial Urinary Sphincter Troubleshooting. Urology, 58 :779-782, 2001.

F. Maillet, J-M. Buzelin, O. Bouchot, and G. Karam; "Management of Artificial Urinary Sphincter Dysfunction"; European Urology, 46 :241-246, 2004.

K. Takayama, S. Kitada, and J. Kumazawi; "New Method for Measuring Bladder Pressure"; Urology, 29 :632-634, 1987.

R. Villet, C. Fitremann, D. Salet-Lizee, D. Collard, and M. Zafiropulo; "Un Nouveau Procédé De Traitement De Isincontinence Urinaire Dseffort : Soutènement Sous-Urétral Par Une Bandelette De Prolèneô Sous Anesthésie Locale"; Progrès en Urologie, 8 :1080-1082, 1998.

P. McBeth et al. "Effect of Patient Positioning on Intra-Abdominal Pressure Monitoring", The American Journal of Surgery 193 (2007) 644-647.

European Office Action of EP Patent No. 08787000 dated Jan. 17, 2012.

McBeth, Paul et al., "Effect of patient positioning on intra-abdominal pressure monitoring", pp. 644-647 (2007), published by The American Journal of Surgery 193.

* cited by examiner

DEVICE TO PREVENT URINARY LEAKAGE

CROSS REFERENCE TO RELATED APPLICATIONS

This application is a National Phase of PCT/EP2008/060404 filed Aug. 7, 2008, which claims priority to FR 0757159 filed Aug. 24, 2007.

BACKGROUND OF THE INVENTION

Field of the Invention

The present invention concerns devices for the artificial regulation of the flow of human fluids, and more precisely devices intended to prevent urinary incontinence.

State of the Art

Urinary incontinence is a handicap which affects both women and men. This handicap can be defined as involuntary loss of urine through the urethra. In most cases, it is due to weakening of pelvic support or of the bladder/sphincter unit.

Depending on symptoms, solutions exist which do not require any surgery, such as rehabilitation or medicinal treatments. When these methods are insufficient, severe incontinence then requires the insertion of a prosthesis so that the patient can return to a normal social life. In the event of severe incontinence, the method the most frequently used consists of implanting an artificial urinary sphincter (AUS, or SUA referring to the French expression "Sphincter Urinaire Artificiel").

The most widespread prosthesis consists of a hydraulic system in silicon elastomer formed of three main parts. The first part consists of an occlusive cuff placed around the urethra and exerting urethral circumferential pressure by means of a pad filled with liquid and thereby ensuring patient continence. The second is a pressure regulating balloon which, when filled with a certain volume of liquid (around 20 ml), allows constant hydraulic pressure to be set up. The regulated pressure is chosen in relation to the patient during surgery, it not being possible to change this pressure once the prosthesis is in place. Finally, a pump is needed to ensure opening of the urethral part compressed by the cuff. This pump consists of a bulb, a resistor and two valves which ensure circulation of the liquid to or from the occlusive cuff. When the person feels the urge to urinate, such person presses on the bulb located on the lower part of the pump, the fluid is transferred from the cuff to the regulating balloon: the pressure exerted on the urethra then becomes negligible compared with the bladder pressure. The urine is then able to flow freely outside the bladder, meaning that this is a non-dysuric method. A few minutes later, the liquid is transferred from the balloon to the cuff by means of the pressure exerted on the resistor by the regulating balloon, the urethra is again occluded. The control pump is positioned in the scrotum in men and in one of the labia in women.

The efficiency of this prosthesis means that it is a reference product but it nevertheless has a certain number of disadvantages. Firstly, as mentioned above, the regulating pressure of the cuff can only be adapted at the time of implanting of the prosthesis, which may give rise to problems if the development of the pathology leads to requiring modification of pressure at the urethra to meet the patient's needs. Additionally, this system does not offer satisfactory comfort for the patient who must actuate the pump whenever necessary, such control not being easy moreover since the pump must be held and forcefully pressed. Finally, the functioning of this prosthesis entails almost continuous major compression of the urethra, which may induce urethral atrophy. Since the prosthesis only operates at one single urethral pressure, this must be fairly high to prevent leaks, which over the long term may damage the urethra. Finally, there are problems of reliability of the constituent parts of the prosthesis, notably the pump and hydraulic circuit assembly.

Alternative devices have been developed in an attempt to overcome some of these drawbacks, in particular by proposing electronic controls for the prosthesis, but none has proved satisfactory, notably with regard to their use or patient safety.

The above-mentioned disadvantages related to existing artificial urinary sphincters means that these prostheses are only used to treat major urinary incontinence. As a result, artificial urinary sphincters are not used for patients suffering from minor incontinence, i.e. generally only stress incontinence. These patients prefer to bear the discomfort of their pathology or opt for a dysuric prosthesis i.e. a prosthesis which constantly exerts pressure on the urethra. For voiding to be possible, the patient must contract the bladder sufficiently to combat the resistance set up at the urethra by the prosthesis. In addition to the drawback mentioned above concerning almost constant pressure applied to the urethra which may lead to urethral atrophy, the effort required for voiding with this type of prosthesis creates a kind of artificial prostate adenoma which may have consequences for the patient.

One purpose of the present invention is therefore to propose a device to prevent urinary leakage in a patient, which solves at least one of the above-mentioned disadvantages.

One purpose of the present invention is more particularly to propose a device to prevent urinary leakage whose functioning reduces mean compression at the urethra to prevent its deterioration.

Another purpose of the invention is to propose a device to prevent urinary leakage that is simple and reliable, and can therefore be used irrespective of the seriousness of the urinary incontinence to be treated.

DISCLOSURE OF THE INVENTION

For this purpose, a device is proposed to prevent urinary leakage intended to be implanted in a patient, comprising:
  compression means to compress the urethra of the patient,
  electronic control means to actuate the compression means,
characterized in that it further comprises measurement means, to measure the activity of the patient, coupled with control means, the control means functioning along a predictive model of urinary leakage based on patient activity so as to anticipate any leakage of urine in relation to the measured activity of the patient.

Preferred but non-limiting aspects of the device to prevent urinary leakage are the following:
  the measurement means comprise means to measure the position and movement of the patient, said means to measure the position and movement of the patient possibly comprising an accelerometer with one or more measurement axes;
  the measurement means comprise means to measure the intra-abdominal pressure of the patient;

the measurement means comprise means to measure the intra-vesical pressure;

the measurement means comprise means to measure the endo-urethral pressure of the patient;

the measurement means comprise means to measure the activity of a muscle;

the means to measure the activity of a muscle comprise a MMG sensor (mechanomyograph) intended to be placed on said muscle to measure the movements generated at the time of the contractions of said muscle;

the means to measure the activity of a muscle comprise an EMG sensor (electromyograph) intended to be placed through said muscle to measure the electric potential generated on contractions of said muscle;

the means to measure the activity of a muscle comprise means to measure the activity of at least one portion of one of the rectus abdominis muscles, to measure the activity of at least one of the pelvic muscles and/or to measure the activity of the detrusor;

the measurement means comprise means to measure the patient's heart rate;

the measurement means comprise means to measure the patient's respiratory rate;

the device is characterized in that it further comprises:
detection means intended to be arranged in the patient to detect urinary leakage;
storage means to store measurement and detection signals provided by the measurement means and the detection means respectively,
processing means to process measurement and detection signals stored for a determined time corresponding to a significant period of activity of the patient, to construct a predictive model of urinary leakage in the patient, by correlating a combination of all or part of the measurement signals with the presence or absence of subsequent urinary leakage, so that the predictive model can be used to anticipate any urinary leakage in relation to the measured activity of the patient;

the device further comprises means to measure filling of the patient's bladder, the predictive model of urinary leakage being further based on filling of the patient's bladder;

the means to measure filling of the bladder comprise an ultrasound sensor intended to be implanted in the patient to visualize the bladder;

the control means comprise means to actuate the compression means dynamically in relation to the measured activity of the patient;

the compression means are adapted to exert compression of variable intensity on the urethra, ranging from no compression to full occlusion of the urethra;

the device further comprises safety means adapted to actuate the compression means to obtain full absence of compression on the urethra in response to instructed opening and, in response to instructed closing, to actuate the compression means to obtain compression of the urethra equal to the compression prior to the opening instruction given by the patient;

the safety means are coupled with physiological sensors intended to be implanted in the patient to allow the patient to transmit an opening or closing instruction to the safety means;

the physiological sensors are arranged for measurement of the contraction of a muscle so that the instruction to open or to close is related to the frequency of contraction of said muscle;

the safety means are coupled with external control means adapted to allow an assistant to transmit an opening or closing instruction to the safety means;

the safety means are able to be actuated by the external control means via radio waves;

the safety means are able to be actuated by the external control means via magnetic waves;

the safety means are coupled with an internal clock, the internal clock permitting the recording of time periods between micturitions of the patient, the safety means being adapted to actuate the compression means to obtain full absence of compression on the urethra if the maximum time period between two micturitions is exceeded.

A method is also proposed to control a device for the prevention of urinary leakage intended to be implanted in a patient, said device comprising means to compress the urethra of the patient, electronic control means to actuate the compression means, the method being characterized in that it comprises the steps consisting of:
measuring the patient's activity with the measurement means,
comparing the patient's measured activity with a predictive model of urinary leakage based on the patient's activity,
controlling the compression means in relation to the measured activity and to the predictive model in order to anticipate any urinary leakage.

Preferred but non-limiting aspects of this control method are the following:
the method further comprises the prior steps consisting of:
for a determined time corresponding to a significant period of activity of the patient, measuring the activity of the patient with the measurement means, and recording the corresponding measurement signals,
simultaneously, detecting urinary leaks using detection means arranged in the patient to detect any urinary leakage, and recording the corresponding detection signals,
determining the trend in measurement signals preceding each detected urinary leakage,
constructing a predictive model of the patient's urinary leakage, by correlating a measurement signal given in the presence or absence of a subsequent urinary leak, so that the predictive model is able to anticipate any urinary leak in relation to the measured activity of the patient;

the method further comprises a step consisting of measuring filling of the patient's bladder, the urinary leakage predictive model being further determined in relation to filling of the bladder;

in response to an opening instruction, the compression means no longer exert any compression on the urethra, and in response to a closing instruction, the compression means exert a compression on the urethra that is equal to the compression preceding the opening instruction given by the patient, the patient being able to give an opening or closing instruction via a physiological signal.

DESCRIPTION OF THE FIGURES

Other characteristics and advantages of the invention will become further apparent from the following description which is given solely by way of illustration and is non-limiting, and is to be read with reference to the appended drawings in which.

DETAILED DESCRIPTION OF THE INVENTION

Known prostheses to overcome urinary incontinence generally exert constant pressure on the urethra except at the time of micturition when the pressure is relaxed to allow unrestricted voiding.

However, for a healthy patient, the sphincter has dynamic functioning, i.e. it exerts greater or lesser pressure on the urethra in relation to needs. The demand placed on the sphincter is effectively greater or lesser depending on the activity exerted by the patient, but also in relation to the filling of the bladder i.e. the volume of urine in the bladder).

The device proposed herein, which is described in detail below, reproduces this dynamic functioning of the sphincter, making it possible to vary the pressure on the urethra in relation to the patient's activity, so as to reduce the mean pressure applied to the urethra.

The operating principle of the described device to prevent urinary leakage is the monitoring of the patient activity using different sensors so that it is possible, using a predictive model, to anticipate any possible urinary leak related to increased intra-vesical pressure compared with urethral pressure, and to apply pressure to the urethra whenever necessary to prevent these leaks.

Figure 1:
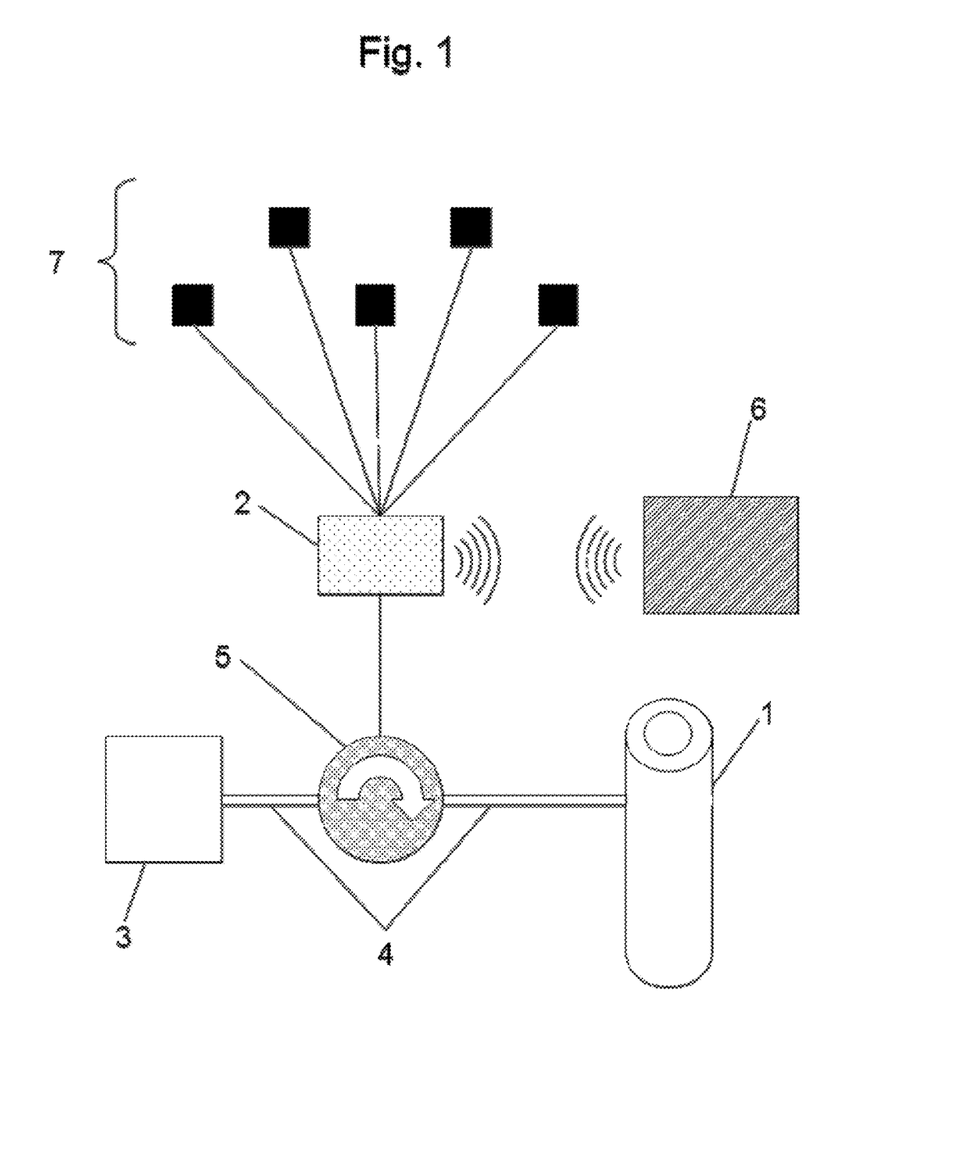
FIG. 1 is a schematic illustration of the device to prevent urinary leakage according to the invention.

As can be seen illustrated in FIG. 1, the device to prevent urinary leakage comprises an occlusive cuff 1 intended to be placed around the urethra of the patient to be treated.

The device presented is electronically controlled and therefore comprises an electronic control box 2 comprising at least one microprocessor.

This control box 2 is used to actuate the cuff 1 so that it applies greater or lesser pressure to the urethra. The actuation of the cuff 1 may be of any type, both hydraulic and mechanical.

In the example illustrated in FIG. 1, the cuff 1 is coupled with a hydraulic actuation circuit comprising a reservoir 3 and ducts 4 for circulation of a fluid. This hydraulic circuit further comprises means 5 to circulate the fluid enabling the fluid to circulate from the reservoir 3 to the cuff 1 and the reverse.

These circulation means 5 are adapted for fluid circulation at relatively high rates of several tens of milliliters per minute. The fluid must be circulated rapidly in the hydraulic circuit so that the cuff can be brought to the desired pressure in a relatively short time, in the order of 100 ms.

It is possible for example to use a micropump as circulation means 5. To increase the performance of the micropump if necessary it is possible to place an overpressure chamber at the outlet of the pump and a microvalve with proportional control at the input to the cuff, which will allow the required pressure to be reached in a shorter time. Another solution is to use as circulation means 5 a piston system actuated by a micromotor, the piston enabling the liquid to be injected quicker into the cuff and thereby reach the desired pressures.

The control device 2 further comprises means for remote communication with an external control device 6. This communication can be made via radio waves, using technology of Bluetooth© type for example. This will allow modification to the parameterization of the control device, even to take control thereof to force the functioning of the device to prevent urinary leakage.

Finally, the device comprises a plurality of sensors 7 allowing the patient's activity to be measured. These sensors 7 may be of any type; an accelerometer may be used for example to measure movements of the patient, MMG (mechanomyograph) or EMG (electromyograph) sensors to measure the activity of some of the patient's muscles, or pressure sensors (abdominal, urethral, even intra-vesical when this is possible).

The choice of sensors 7 is explained in more detail in the remainder of the description. It is noted however that the sensors used do not actually require any surgery to be placed in position. They may simply be placed in some parts of the abdomen.

These sensors 7 will be used during the calibration phase of the device, during which a predictive model of urinary leakage will be constructed. They will also come into use during normal utilisation of the device to prevent urinary leakage by causing the pressure of the cuff 1 to vary on the urethra whenever it is necessary.

The predictive model of urinary leakage is designed to anticipate a urinary leak which may be suffered by the patient, based on information concerning the activity of the patient. Some particular activities effectively lead to a change in the ratio between intra-vesical pressure and urethral pressure, which may cause undesired urinary leaks. This is the case for example if the patient exerts an effort that is greater than normal activity. It is also the case when the patient is in sleep phase when urethral pressure is reduced as compared with intra-vesical pressure. Detection of these particular situations therefore makes it possible to anticipate any possible leak and therefore to modify the pressure exerted on the urethra.

To avoid causing the pressure on the urethra to vary continuously, focus is given to 4 main phases during which pressure on the urethra must be modified.

First there is the voiding phase, when the sphincter applies little or no pressure on the urethra so that a patient is able to urinate freely without any particular effort. During this voiding phase, very low pressure can be applied to the urethra, corresponding for example to a pressure $P_0$ in the cuff that is less than 10 cmH$_2$O (10 centimeters of water).

As already indicated, another important phase is the sleep phase during which the body relaxes. The corresponding pressure $P_{lying}$ may be relatively low even close to $P_0$ in some cases. It is noted that this pressure is patient-dependent and may be determined on a case-by-case basis once the device has been implanted.

The most frequent phase corresponds to the time when the patient leads normal activity i.e. during which no particular effort is made (standing up, sitting down, walking, etc.). In this case, a pressure $P_{act}$ must be applied to the urethra. This pressure is to be determined during calibration of the device so that it is just sufficient to prevent leaks.

The last phase corresponds to the time when the patient exerts an effort involving high intra-vesical pressures (exercising, coughing, etc.). The pressure $P_{effort}$ exerted on the urethra in this case is higher than pressure $P_{act}$. The pressure $P_{effort}$ can be used to modulate $P_{act}$, when there is a sudden increase in pressure in the patient's bladder when conducting normal activity; for example after coughing the pressure in the cuff increases from $P_{act}$ to $P_{effort}$ for one instant then falls back to $P_{act}$ if bladder pressure has been reduced.

Evidently, patient activity and associated sphincter pressure could be broken down into other phases. The proposed device is described for dynamic control over pressure at the urethra according to these 4 phases, even if it could easily be adapted for another breakdown of patient activity.

A description will now be given of the sensors 7 which can be used alone or in combination to measure patient activity so that it is possible to compare this information with the predictive model of urinary leakage and to cause the pressure of the cuff to vary on the urethra accordingly.

As already pointed out, preference is given to sensors which do not require any particular surgery to place them in position. It is further noted that it is also possible to use sensors already implanted in the patient, or which are to be implanted later for other devices. For example, if a pacemaker is or is to be implanted, it is possible to cause it to communicate with the described artificial urinary sphincter, in particular to use data on the patient's heart rate. In this case, a standard data transfer protocol between the devices can be used.

It may first be of interest to measure the position and movement of the patient.

For this purpose, it is possible for example to use an accelerometer comprising one or more measurement axes. Preferably, an accelerometer having three measurement axes is used so that it is possible to evaluate patient movements in the three directions in space.

Figure 2:
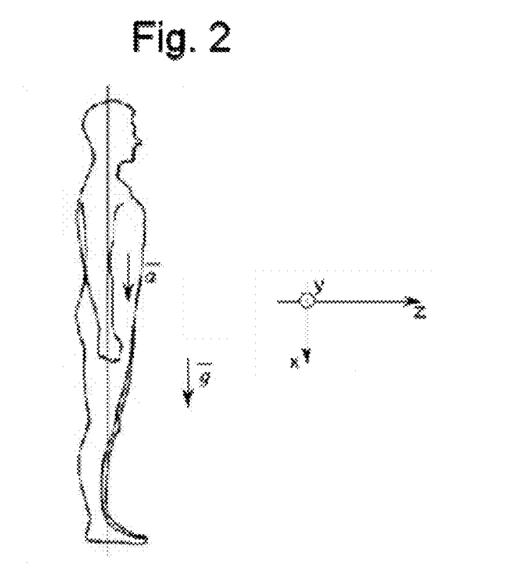
FIG. 2 illustrates the use of an accelerometer in a patient for the device shown in FIG. 1.

It is possible to limit the number of measurement axes to one, the accelerometer then being arranged so that the measurement axis lies in the longitudinal axis of the patient i.e. following axis x such as illustrated in FIG. 2.

An accelerometer with only one measurement axis can effectively measure the inclination of the patient by means of earth's gravity and thereby detect when a person is lying down. It also provides information on patient movements which lead to an increase in intra-vesical pressure even if this information is incomplete since only one direction of movement is detected.

Figure 3:
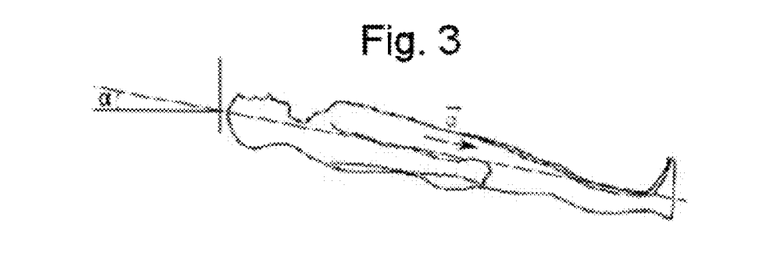
FIG. 3 illustrates measurement of the inclination of a patient provided with an accelerometer as shown in FIG. 2.

Regarding detection of the lying down position, if it is considered that the force of gravity $\vec{g}$ follows axis x (see FIG. 2), simple measurement of acceleration $\vec{a}_x$ following this axis can determine whether the patient is lying down. If it is estimated that a person is lying down when $\alpha<10°$ (see FIG. 3), an amplitude $|\vec{a}_x|=9.81 \sin(10)=1.7$ m/s$^2$ is obtained i.e. around environ 0.17 g, which we will take to be our detection threshold.

The consideration given to the time during which the amplitude of acceleration is less than 0.17 g is also significant since this amplitude can also be less than the determined threshold even though the patient is not lying down. This is the case for example when the patient undergoes relative accelerations following the negative $x_s$ (reference system in FIG. 2) for a short time e.g. when in a lift or when jumping. Therefore the time must be calculated during which acceleration is less than the threshold of 0.17 g so as to confirm a stable lying down status, and to actuate the system so that the pressure in the cuff changes to pressure $P_{lying}$.

The accelerometer is also used as actimeter to measure accelerations along axis x which depend on patient movements. As mentioned above, persons suffering from stress incontinence (little severe incontinence) often suffer from leaks during activities which lead to an increase in abdominal, vesical and urethral pressure related to the pressure forces exerted by the surrounding organs. These leaks again depend on several factors related to movements of the patient. Measurement of patient movement gives additional information for estimation of the required cuff pressure and in particular allows determination of transition from pressure $P_{act}$ to pressure $P_{effort}$ which takes place when the patient is exerting an effort such as a sports activity for example or when going down stairs.

Measurements were made with the accelerometer during various patient activities in order to determine the threshold for accelerometric measurement allowing differentiation between "normal" activity and activity with "effort". The accelerometer sensor with one axis was placed on the abdomen of a person when walking, running and jumping and the data was recorded during these activities. The table below describes the accelerations noted during the different exercises, and it will be noted that when the patient is standing without moving with the accelerometer directed in the direction of the $x_s$ (according to the reference system in FIG. 2), the measurement is negative since the mobile weight used in the accelerometer undergoes the force of earth's gravity.

| Posture/activity | Acceleration (g) |
| --- | --- |
| Standing | −1 |
| Lying down | 0 |
| Walking | ±0.5 |
| Running | >|0.7| |
| Jumping, low amplitude | >|0.7| |
| Jumping high amplitude | >|1.5| |
| Stairs (descending) | ≈|0.7| |

Figure 4:
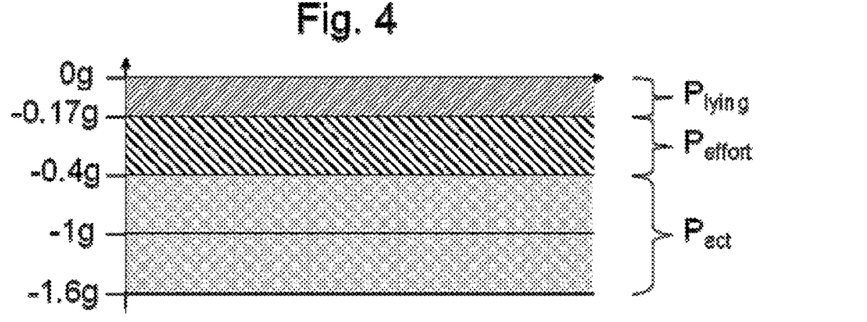
FIG. 4 illustrates the trigger thresholds of the accelerometer for the device shown in FIG. 1.

These different measurements made it possible to determine several trigger thresholds with which to relate a measured acceleration with a type of activity, and hence with an associated cuff pressure.

Other types of sensors which can be used are pressure sensors.

It is known that leaks depend on intra-vesical pressure. The simplest means to construct the predictive model and then to modify cuff pressure is to measure this intra-vesical pressure. However, placing intra-vesical sensors in position is not easy, which leads to using other types of complementary or substitute sensors.

The implanting of a pressure sensor between the pubic bone and the vesical wall allows indirect measurement of pressure in the bladder. The measurements of this pressure sensor set in the vesical wall provide good correlation with actual intra-vesical pressure. Despite the small measurement amplitudes, it is therefore possible to obtain the values of intra-vesical pressure from this particular sensor.

It has also been evidenced that abdominal pushing leads to increased vesical pressure which, on and after a certain threshold of abdominal pressure can lead to urinary leakage. It is therefore of advantage to use an abdominal pressure sensor so that it is possible to anticipate any urinary leak. It is to be noted that the threshold value of abdominal pressure corresponding to urinary leakage depends on the volume of bladder filling. Therefore, calibration of the threshold value of abdominal pressure corresponding to urinary leakage may be made by taking into consideration a mean filling value of the bladder. As will be seen further on, it is also possible to provide a system with which to measure or estimate the bladder filling rate, thereby giving threshold values of abdominal pressure in relation to bladder filling.

Determination of the threshold value(s) of abdominal pressure for urinary leakage can be made as follows. The pressure of the cuff is set at $P_{act}$ and the patient is requested to push on the abdomen, glottis closed, in gradually increasing manner until a leak is observed (the pressure in the cuff remains at $P_{act}$). At this moment, the value of abdominal pressure is recorded and will correspond to the threshold abdominal pressure $P_{abdoseuil}$ (from which a margin will be deducted) which will trigger the changeover of the occlusive cuff from $P_{act}$ to $P_{effort}$. This exercise is carried out for different bladder filling volumes, which will provide a threshold value $P_{abdoseuil}$ related to the estimated volume.

A urethral pressure sensor may also be provided. The purpose is essentially safety-related to determine an abnormal increase in urethral pressure, for example at the time of inserting an endo-urethral probe, so that the cuff can be actuated to release constraint on the urethra allowing unrestricted passing of the probe. For this purpose, a pressure sensor can be used for example that is located on the wall of the cuff in contact with the urethra, in order to monitor the variations in pressure at the urethra. Any major increase in pressure would effectively be a sign that an object is probably being inserted through the urethra.

Measuring muscle activity also permits the prediction of any urinary leaks. For this purpose, MMG (mechanomyograph) sensors can be used, intended to be placed on the muscle of interest to measure movements generated by the contractions of said muscle. It is also possible to use EMG sensors (electromyograph) intended to be placed through a muscle to measure the electric potential generated on contraction of the said muscle.

Continence in a healthy person is met by muscle synchronization, in particular between the rectus abdominis muscles of the abdomen and the pelvic floor. It has been shown that the time between an increase in intra-vesical pressure and an increase in intra-urethral pressure is $t_p \approx 250$ ms±100 ms with urethral pressure exceeding abdominal pressure. This means that there exists anticipation of contraction by the urinary sphincter with any sudden increase in abdominal pressure to avoid leakage. When coughing for example, the sphincter contracts when the urge to cough is felt.

If sensors are used implanted on at least one portion of one of the rectus abdominis muscles, and if it is estimated that the mechano-electric feedback (i.e. the time between start of electric activity of the muscle and the start of mechanical activity) is of the same order as $t_p$, it is then possible to predict sudden increases in bladder pressure.

Measurements of the activity of the detrusor, which is the muscle forming the bladder, also give information that can be directly used to anticipate urinary leakage.

The pelvic floor, together with the pelvic bones, forms the bottom part of the abdominal cavity; it partly contains the urethra and is formed of a complex group of muscles, ligaments and nerves. At the time of physical effort, it is this assembly of organs which ensures continence in a healthy person. Reducing urinary leakage in a person suffering from little severe incontinence, such as stress incontinence, is possible after rehabilitation of the pelvic floor. This rehabilitation translates chiefly as muscular exercise directed at strengthening the tonicity of the pelvic floor. The results obtained after rehabilitation have shown an increase in the strength of the perineal muscles and good improvement in incontinence in women suffering from stress incontinence. Along the same lines as rehabilitation of the perineum, we propose implanting an EMG probe to acquire perineal muscle contractions whose duration and amplitude are correlated with the set pressure for the cuff. Specific rehabilitation of the pelvic floor enables a patient, by means of the muscular contractions made, to control the system so that the pressure in the cuff changes to $P_{effort}$ when a leak is felt. The purpose is to provide an additional parameter for the system in the particular case when it does not respond to the instruction to avoid this leak. It can be imagined for example that if the patient feels a urinary leak, the patient contracts the perineal muscles which brings the pressure in the cuff to $P_{effort}$ and thereby stops the leak. The contraction of the perineal muscles is a natural reflex when the urge for voiding is increasingly felt. Therefore, the "control" over the pressure of the cuff in relation to the activity of the pelvic floor does not require any complicated rehabilitation difficult to be assumed by the patient.

The EMG of the pelvic floor can also be used to command opening of the prosthesis (passing of cuff pressure to $P_0$) when the patient contracts the perineum muscles x times every y seconds. The sequence of contractions of the perineal muscles which permits opening of the cuff must be sufficiently complex to avoid obtaining the same sequence involuntarily, but it must also be sufficiently simple for reproducibility of the sequence of contractions.

As indicated above, knowledge of filling of the bladder can be a parameter of interest to take into account, notably to increase the precision of correlation between sensor measurements and predicted leakage.

After complete micturition, the bladder is almost empty and it is therefore not necessary to apply the same pressure to the urethra as when the bladder is full, whether for $P_{act}$ or for $P_{effort}$. This is why the two pressure values $P_{act}$ and $P_{effort}$ increase over time after voiding until they reach the previously determined thresholds (to arrive at $P_{actmax}$ and $P_{effortmax}$ just P before the following voiding).

Real measurement of bladder filling is difficult to implement. It is possible however to estimate filling of the bladder. The frequency of voiding (estimated at around 4 to 5 times per 24 h with no nocturnal voiding in a healthy person) is recorded, which allows an estimation of the mean bladder filling time i.e. the time between almost zero vesical pressure and pressure $P_{actmax}$ for so-called "normal" patient activity. This gives a mean time $T_{moy}$ such that:

$$T_{moy} = \sum \frac{T_m(i)}{k}$$

in which $T_m(i)$ is the $i^{th}$ time recorded between two voidings (i ranging from 1 to k) and k is the number of voiding times recorded.

Initially, i.e. after implantation, the time $T_{moy}$ is of short duration, and can optionally be estimated in relation to the patient. Then, as and when recordings are made, $T_{moy}$ will increasingly correspond to the mean time between each micturition of the patient. It is obvious that, depending on patient activity and hydration, filling of the bladder takes place at a quicker or slower rate. However, the pressure exerted on the urethra will always be sufficient since consideration is given to a greater margin for applied pressure and to adjustments made beforehand by care personnel on necessary closing pressures. Assuming that the frequency of voiding follows a Gaussian law, it is possible for example to increase the set pressure values linearly until they reach their maximum at $T_{moy}$-a, in which a is the standard deviation of our function.

One alternative to estimate the extent of filling of the bladder consists of using a miniature ultrasound sensor, for example constructed with CMUT technology i.e. using a capacitive micromachined ultrasonic transducer. The bladder is effectively characterized by low echogenecity. The sensor is implanted so that observation of the bladder is possible. Ideally two-dimensional (even three-dimensional) observation is made, but it is to be noted that one-dimensional observation may provide sufficient information. The advantage of observation in a single direction is that data processing (which consists for example of measuring the number of points whose echogenecity lies below a certain threshold) is extremely simple and requires very little computing. This number of points can be correlated with the extent of filling of the bladder. The correlation function can initially be estimated and then fine-tuned during use of the device by the patient, through analysis by the patient and by the medical team of the results obtained from processing ultrasound data in relation to clinical observations (urinary leaks for example) or analysis of measurements of the extent of filling of the bladder or by other means (external ultrasound performed by a doctor during a consultation for example).

It will be noted that by taking into account the rate of filling of the bladder, the energy consumption of the system is also reduced since less demand is placed on the actuators.

The main function of the sensors described in detail above is to permit the construction of a predictive model of urinary leakage, which will be used to manage changes to pressure on the urethra in relation to patient activity.

However, these sensors can also be used to control the described device to prevent urinary leakage. When the patient wishes to urinate, the device must be instructed so that the cuff reaches a pressure of $P_0$ allowing unrestricted voiding. Rather than using a mechanical actuator, the sensors can be used to transmit a voiding signal given by the user to the control device 2.

This alternative was already described above with respect to sensors to sense activity of the pelvic muscles. It is effectively possible to programme the control device 2 so that it actuates the device to obtain a voiding pressure $P_0$ in response to a particular succession of signals derived from the EMG sensor of the pelvic muscles.

This can be achieved with most of the other sensors.

It is also useful that an assistant or other person should be able to actuate the device to prevent urinary leakage should the patient no longer be capable of actuating it alone or for any other reason.

As indicated above, the control device 2 is preferably adapted for wireless communication with an external control device 6. This external control device may for example be adapted to instruct the control device 2 to actuate the cuff 1 in order to obtain a voiding pressure $P_0$.

Any type of communication can be envisaged such as a radiofrequency communication.

One alternative or complementary solution is to use the sensors as controls to command opening of the device, in the same way as is provided for the patient. For example by using an abdominal pressure sensor and by programming a particular opening sequence, an assistant may command opening of the artificial urinary sphincter by tapping the particular sequence on the abdomen.

The system can also be provided with a safety valve which can be actuated by a magnetic field, and which is adapted to place the cuff under a pressure permitting voiding when actuated by a particular external magnetizing system. The use of a magnetizing system has the advantage of permitting opening without requiring any energy consumption.

The device to prevent urinary leakage presented here offers numerous advantages for the treatment of urinary incontinence, irrespective of its seriousness.

Ease of controls and the safety aspects are firstly important for user comfort.

In addition, automation of the prosthesis through the use of electronic control means that can be remotely adjusted by an external device offers the possibility to adjust the settings of the device without having recourse to surgery, which is particularly advantageous when it is known that necessary pressure constraints at the urethra or the threshold pressure values for leaks can change over time.

Finally, the most substantial advantage lies in the dynamic functioning permitted by the described device. The fact that it is possible to apply pressure to the urethra in relation to the patient's real needs, in relation to the activity of the patient, places less demand on the urethra, and thereby reduces risks of urethral atrophy.

By way of illustration, giving consideration to a prior art artificial urinary sphincter applying a pressure in the order of 70 cmH$_2$O when actuated, and assuming the voiding frequency of the patient is around 4 times per 24 hours and that each voiding lasts around 3 minutes during which time the opening of the cuff is almost zero, the mean pressure applied to the urethra is around 69.8 cmH$_2$O. If the same parameters are considered for the prosthesis presented herein, with pressures after implantation set at $P_{lying}$=30 cmH$_2$O for 30% of the time, $P_{act}$=45 cmH$_2$O 50% of the time and $P_{effort}$=70 cmH$_2$O for the remaining 20%, the mean pressure obtained in the cuff is approximately 45.5 cmH$_2$O i.e. a reduction in the pressure applied to the urethra of almost 36%.

The reader will appreciate that numerous modifications can be made hereto without departing materially from the novel teachings and advantages described herein. Therefore any modifications of this type are intended to be incorporated within the scope of the described device to prevent urinary leakage.

The invention claimed is:

1. A device to prevent urinary leakage intended to be implanted in a patient, comprising:
    an occlusive cuff to compress the urethra of the patient,
    an electronic controller to actuate the occlusive cuff,
    at least one sensor to measure at least one activity of the patient that precedes the occurrence of a urinary leakage and coupled with the electronic controller, wherein the at least one sensor comprises an accelerometer having at least one measurement axis adapted to measure an acceleration of the patient,
    the electronic controller being configured to:
        determine a position and a movement of the patient based on the acceleration of the patient and a period of the acceleration,
        operate in accordance with a predictive model of urinary leakage to anticipate a possible urinary leak based on the position and movement of the patient, wherein the predictive model correlates data from the accelerometer with a type of activity of the patient and determines a pressure to be exerted by the occlusive cuff depending on the type of activity, so as to vary the pressure exerted by the occlusive cuff in relation to the measured position and movement of the patient to prevent any urinary leakage, and
        vary the pressure to at least two non-zero predetermined pressures, each predetermined pressure being specific to a type of activity of the patient.

2. The device of claim 1, wherein the at least one sensor further comprises a sensor adapted to measure intra-abdominal pressure of the patient.

3. The device of claim 1, wherein the at least one sensor further comprises a sensor adapted to measure intra-vesical pressure of the patient.

4. The device of claim 1, wherein the at least one sensor further comprises a sensor adapted to measure endo-urethral pressure of the patient.

5. The device of claim 1, wherein the at least one sensor further comprises a sensor adapted to measure activity of a muscle of the patient.

6. The device of claim 5, wherein the at least one sensor adapted to measure the activity of the muscle comprises a mechanomyograph sensor intended to be placed on the muscle to measure movements generated by contractions of the muscle.

7. The device of claim 5, wherein the at least one sensor adapted to measure the activity of the muscle comprises an electromyograph sensor intended to be placed through the muscle to measure the electric potential generated by contractions of the muscle.

8. The device of claim 5, wherein the at least one sensor adapted to measure the activity of the muscle comprises a sensor adapted to measure the activity of at least one portion of a rectus abdominis muscle of the patient.

9. The device of claim 5, wherein the at least one sensor adapted to measure the activity of the muscle comprises a sensor adapted to measure the activity of at least one pelvic muscle of the patient.

10. The device of claim 5, wherein the at least one sensor adapted to measure the activity of the muscle comprises a sensor adapted to measure activity of a detrusor of the patient.

11. The device of claim 1, wherein the at least one sensor further comprises a sensor adapted to measure heart rate of the patient.

12. The device of claim 1, wherein the at least one sensor further comprises a sensor adapted to measure respiratory rate of the patient.

13. The device of claim 1, wherein the electronic controller configured to actuate is the occlusive cuff dynamically depending on the measured activity of the patient.

14. The device of claim 1, wherein the occlusive cuff is configured to apply compression of variable intensity to the urethra, ranging from absolutely no compression to full occlusion of the urethra.

15. The device of claim 1, wherein the electronic controller is adapted to actuate the occlusive cuff to obtain full absence of compression on the urethra in response to an opening instruction, and in response to a closing instruction to actuate the occlusive cuff to obtain compression of the urethra equal to the compression prior to the opening instruction given by the patient.

16. The device of claim 15, wherein the electronic controller is coupled with a physiological sensor intended to be implanted in the patient, so as to enable the patient to transmit an opening or closing instruction in the form of a physiological signal generated by the patient to the electronic controller.

17. The device of claim 15, wherein the electronic controller is coupled with an external controller adapted to allow an assistant to transmit an opening or closing instruction to the electronic controller.

18. The device of claim 17, wherein the controller is adapted to communicate with the external controller via radio waves.

19. The device of claim 17, wherein the controller is adapted to communicate with the external controller via magnetic waves.

20. The device of claim 15, wherein the electronic controller is coupled with an internal clock, the internal clock allowing the recording of the time intervals between patient voidings, the electronic controller being adapted to actuate the occlusive cuff to obtain total absence of compression on the urethra in the event that a maximum time interval between two voidings is exceeded.

21. The device of claim 1, wherein the electronic controller is capable of varying the pressure to each of: a minimal non-zero pressure, a lying pressure, a normal activity pressure, and an effort pressure.

22. The device of claim 1, wherein the electronic controller is configured to vary the pressure to at least three predetermined pressures, each predetermined pressure being specific to a type of activity of the patient.

23. The device of claim 1, wherein the predictive model correlates the data from the accelerometer with the type of activity of the patient so as to break down the patient's activity between at least: a sleep phase, a normal activity phase and a phase of activity involving an effort, and
wherein the electronic controller is configured to vary the pressure to at least three predetermined pressures, each predetermined pressure being specific to a type of activity of the patient.

24. The device of claim 1, further comprising a reservoir for a fluid, wherein the electronic controller is configured to actuate the occlusive cuff by causing the fluid to circulate between the reservoir and the occlusive cuff.

25. The device of claim 1, wherein the electronic controller is configured to:
determine that the patient is lying down when the acceleration of the patient is less than a predetermined acceleration for a predetermined period; and
vary the pressure exerted by the occlusive cuff based on whether the patient is lying down.

26. The device of claim 1, wherein the accelerometer is adapted to measure a static acceleration of the patient and a dynamic acceleration of the patient, and the electronic controller is configured to determine the position and the movement of the patient based on the static and dynamic acceleration of the patient.

27. The device of claim 1 wherein determining the position of the patient includes determining whether the patient is standing or lying down.

28. A device to prevent urinary leakage intended to be implanted in a patient, comprising:
an occlusive cuff to compress the urethra of the patient,
a reservoir for a fluid,
an electronic controller to actuate the occlusive cuff by causing a fluid to circulate between the reservoir and the occlusive cuff,
at least one activity sensor to measure at least one activity of the patient that precedes the occurrence of a urinary leakage and coupled with the electronic controller, wherein the at least one activity sensor comprises an accelerometer having at least one measurement axis adapted to measure a position and a movement of the patient,
a pressure sensor intended to be arranged on the patient to measure an abdominal pressure of the patient in order to detect urinary leakage,
storage medium to store activity and pressure signals respectively derived from the at least one activity sensor and the pressure sensor, and processor to process the activity and pressure signals stored for a determined time corresponding to a period of activity of the patient, in order to construct a predictive model of urinary leakage of the patient by correlating a combination of all or part of the activity signal with the presence or absence of a subsequent urinary leak, so that the predictive model allows anticipation of a possible urinary leak depending on the measured activity of the patient, the electronic controller operating in accordance with the predictive model of urinary leakage to anticipate the possible urinary leak based on the position and movement of the patient, wherein the predictive model correlates data from the accelerometer with a type of activity of the patient and determines a fluid pressure to be applied within the occlusive cuff depending on the type of activity, so as to vary the fluid pressure within the occlusive cuff in relation to the measured position and movement of the patient to prevent any urinary leakage, wherein the electronic controller is capable of varying the pressure to at least two non-zero predetermined pressures, each predetermined pressure being specific to a type of activity of the patient.

29. A device to prevent urinary leakage intended to be implanted in a patient, comprising:

an occlusive cuff to compress the urethra of the patient, a reservoir for a fluid, an electronic controller to actuate the occlusive cuff by causing a fluid to circulate between the reservoir and the occlusive cuff, at least one first sensor to measure at least one activity of the patient that precedes the occurrence of a urinary leakage and coupled with the electronic controller, wherein the at least one first sensor comprises an accelerometer having at least one measurement axis adapted to measure a position and a movement of the patient, wherein the electronic controller is configured to estimate a mean fill time of the bladder of the patient based on a number of voidings by the patient and a plurality of periods that are each between two consecutive ones of the voidings, the electronic controller operating in accordance with a predictive model of urinary leakage to anticipate a possible urinary leak based on the position and movement of the patient and the mean fill time of the bladder of the patient, wherein the predictive model correlates data from the accelerometer with a type of activity of the patient and determines a fluid pressure to be applied within the occlusive cuff depending on the type of activity, so as to vary the fluid pressure within the occlusive cuff in relation to the measured position and movement of the patient to prevent any urinary leakage, wherein the electronic controller is capable of varying the pressure to at least two non-zero predetermined pressures, each predetermined pressure being specific to a type of activity of the patient.

30. A device to prevent urinary leakage intended to be implanted in a patient, comprising:

an occlusive cuff to compress the urethra of the patient, a reservoir for a fluid, an electronic controller to actuate the occlusive cuff by causing a fluid to circulate between the reservoir and the occlusive cuff, at least one sensor to measure at least one activity of the patient that precedes the occurrence of a urinary leakage and coupled with the electronic controller, wherein the at least one sensor comprises an accelerometer having at least one measurement axis adapted to measure a position and a movement of the patient, the electronic controller operating in accordance with a predictive model of urinary leakage to anticipate a possible urinary leak based on the position and movement of the patient, wherein the predictive model correlates data from the accelerometer with a type of activity of the patient and determines a fluid pressure to be applied within the occlusive cuff depending on the type of activity, so as to vary the fluid pressure within the occlusive cuff in relation to the measured position and movement of the patient to prevent any urinary leakage, wherein the electronic controller is capable of varying the pressure to at least two non-zero predetermined pressures, each predetermined pressure being specific to a type of activity of the patient, the electronic controller being adapted to actuate the occlusive cuff to obtain full absence of compression on the urethra in response to an opening instruction, and in response to a closing instruction to actuate the occlusive cuff to obtain compression of the urethra equal to the compression prior to the opening instruction given by the patient, wherein the electronic controller is coupled with a physiological sensor intended to be implanted in the patient, so as to enable the patient to transmit an opening or closing instruction in the form of a physiological signal generated by the patient to the electronic controller, wherein the physiological sensor is arranged to measure the contraction of a muscle so that the opening or closing instruction depends on the frequency of contraction of the muscle.

31. A method to control a device for the prevention of urinary leakage intended to be implanted in a patient, the device comprising an occlusive cuff to compress the urethra of the patient, an electronic controller to actuate the occlusive cuff, and at least one sensor to measure at least one activity of the patient that precedes an occurrence of the urinary leakage and coupled with the electronic controller, which is capable of varying a pressure exerted by the occlusive cuff on the urethra to at least two non-zero predetermined pressures, each of the pressures being specific to a type of activity of the patient, wherein the at least one sensor comprises an accelerometer having at least one measurement axis adapted to measure an acceleration of the patient, the method comprising:

measuring the acceleration of the patient with the at least one sensor, estimating an activity of the patient based on the acceleration of the patient and a period of the acceleration;

comparing the estimated activity of the patient with a predictive model of the urinary leakage to anticipate a possible urinary leak, where in the predictive model correlates data from the accelerometer with a type of activity of the patient and determines a pressure to be applied within the occlusive cuff depending on the type of the activity, and instructing the occlusive cuff to vary the pressure exerted by the occlusive cuff on the urethra in relation to the measured activity and to the predictive model to prevent the possible urinary leak, wherein the pressure exerted can be varied to at least two non-zero predetermined pressures, each predetermined pressure being specific to a phase of activity of the patient.

32. The method of claim 31, further comprising:
for a determined time, corresponding to a period of activity of the patient, measuring the activity of the patient with the at least one sensor, and recording corresponding measurement signals,
simultaneously detecting the urinary leaks with detectors arranged on the patient to detect any leaks, and recording corresponding detection signals,
determining a trend in measurement signals preceding each detected urinary leak,
constructing the predictive model of the urinary leakage of the patient, by correlating a given measurement signal with the presence or absence of a subsequent urinary leak, so that the predictive model can be used to anticipate any urinary leak depending on the measured activity of the patient.

33. The method of claim 32, further comprising: measuring the volume of fluid in a bladder of the patient, the urinary leakage predictive model being further determined based directly on the volume of fluid in the bladder.

34. The method of claim 33 further comprising:
measuring an abdominal pressure of the patient;
increasing the pressure exerted by the occlusive cuff when the abdominal pressure of the patient is greater than a threshold; and
selecting the threshold based on the volume of fluid in the bladder of the patient.

35. The method of claim 31, wherein in response to an opening instruction, the occlusive cuff no longer applies any compression on the urethra, and in response to a closing instruction, the occlusive cuff exerts a compression on the urethra equal to the compression prior to the opening instruction given by the patient, the patient being able to give an opening or closing instruction in the form of a physiological signal generated by the patient that can be sensed by a physiological sensor coupled with the electronic controller.

* * * * *